United States Patent [19]
Ohkawa et al.

[11] Patent Number: 6,069,241
[45] Date of Patent: May 30, 2000

[54] CYTOCHROME P450 GENE

[75] Inventors: Hideo Ohkawa; Hiromasa Imaishi, both of Hyogo-ken, Japan

[73] Assignee: Suntory Limited, Osaka, Japan

[21] Appl. No.: 09/033,055

[22] Filed: Mar. 2, 1998

[30] Foreign Application Priority Data

Mar. 3, 1997 [JP] Japan .................................. 9-047682
Sep. 18, 1997 [JP] Japan .................................. 9-253167

[51] Int. Cl.$^7$ .......................... C12N 15/29; C12N 15/52; C07H 21/02; C07H 21/04
[52] U.S. Cl. ......................................... 536/23.6; 536/23.1
[58] Field of Search .................................. 536/23.6, 24.1, 536/23.1; 435/91.2, 91.5; 800/323.1

[56] References Cited

FOREIGN PATENT DOCUMENTS 0522880A   1/1993   European Pat. Off. .
0 632 128 A1   1/1995   European Pat. Off. .

OTHER PUBLICATIONS

Holton et al, Nature, vol. 366, pp. 276–279, 1993.
Holton et al., "Cloning and expression of cytochrome P450 genes controlling flower colour", Nature , vol. 366, No. 6452, Nov. 18, 1993, pp. 276–279.
Larkin, John C., "Isolation of a cytochrome P450 homologue preferentially expressed in developing inflorescences of *Zea mays*", Plant Molecular Biology, vol. 25, No. 3, Jun. 1994, pp. 343–353.
Toguri et al., "The cloning and characterization of cDNA encoding a cytochrome P450 from the flowers of Petunia a hybrida", Plant Science, vol. 94,, 1993, pp. 119–126.
Nerbert, et al., "The P450 Superfamily: Update on New Sequences, Gene Mapping, and Recommend Nomenclature", DNA and Cell Biology, vol. 10, No. 1, 1991, pp. 1–14.
Nelson, "Cytochrome P450 Nomenclature and Alignment of Selected Sequences", Cytochrome P450: Structure, Mech. and BioChem., 2nd Ed., 1995, pp. 575–606.
The International Society for Plant Molecular Biology, Abstracts of the 4th International Congress of Plant Molecular Biology, Jun. 19–14, 1994, abstract #2071.
Deroles, et al., "Transformation Protocols for Ornamental Plants", Biotechnology of Ornamental Plants, 1997, pp. 87–119.
Holton, et al., "Cloning and expression of cytochrome P450 genes controlling flower colour", Nature, vol. 366, Nov. 18, 1993, pp. 276–279.
Nelson, et al., "The P450 Superfamily: Update on New Sequences, Gene Mapping, Accession Numbers, Early Trivial Names of Enzymes, and Nomenclature", DNA and Cell Biology, vol. 12, No. 1, 1993, pp. 1–51.
Saibo Kogaku, vol. 6, No. 2, 1987, pp. 72–78.

*Primary Examiner*—Lynette R. F. Smith
*Assistant Examiner*—Ashwin D. Mehta
*Attorney, Agent, or Firm*—Pillsbury Madison & Sutro

[57] ABSTRACT

A gene encoding a cytochrome P450 expressed specifically at initial stages in flower-bud growth and a promoter inducing expression of the gene are provided. The cytochrome P450 gene encodes the amino acid sequences encoded by the sequence having the nucleotide 1 to 1488 or the nucleotide 1 to 1617 in SEQ ID NO. 1, and the promoter consists of the base sequence within the nucleotide 1 to 1041 in SEQ ID NO. 4 that is necessary for the promoter activity.

3 Claims, 2 Drawing Sheets

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
        (A) LENGTH: 1722
        (B) TYPE: nucleic acid
        (C) STRANDEDNESS: double
        (D) TOPOLOGY: linear     (xi) SEQUENCE DESCRIPTION: SEQ ID NO: 1:

```
ATG AAT TAT GTA GCA ATT GTA GGT GGA TTA CTA CTT GTC TTG ATT TTA        48
Met Asn Tyr Val Ala Ile Val Gly Gly Leu Leu Leu Val Leu Ile Leu
 1               5                  10                  15

GTT CAA AGT ATT CGT TAC CTA GCA ATA AGC AAC AAA TGT CAC AAA AAG        96
Val Gln Ser Ile Arg Tyr Leu Ala Ile Ser Asn Lys Cys His Lys Lys
                20                  25                  30

CTT CCA CCA GGA CCA ACT CCC CTG CCC TTA ATT GGT AAT TTA CAT AAC       144
Leu Pro Pro Gly Pro Thr Pro Leu Pro Leu Ile Gly Asn Leu His Asn
            35                  40                  45

ACT CTT GGT GCT CAA CCC CAT CAG TCC CTT GCG AAA CTT GCC AAA AAA       192
Thr Leu Gly Ala Gln Pro His Gln Ser Leu Ala Lys Leu Ala Lys Lys
        50                  55                  60

TAT GGT CCA ATT ATT AGC CTC AGG TTG GGC CAA ATT ACG ACA GTG GTT       240
Tyr Gly Pro Ile Ile Ser Leu Arg Leu Gly Gln Ile Thr Thr Val Val
 65                  70                  75                  80

ATA TCT TCA CCA ACA ATG GCT AAA GAA GTC TTA CAA AAA CAA GAT TTA       288
Ile Ser Ser Pro Thr Met Ala Lys Glu Val Leu Gln Lys Gln Asp Leu
                85                  90                  95

GCC TTC TCC AGT AGA ACA ATT CCA AAT GCA CTC CAT GCT CAT AAT CAT       336
Ala Phe Ser Ser Arg Thr Ile Pro Asn Ala Leu His Ala His Asn His
                100                 105                 110

TAT CAA TAC TCT GTT GTA TGG CTA CCA GTT GCT GCT AGA TGG AGA AGC       384
Tyr Gln Tyr Ser Val Val Trp Leu Pro Val Ala Ala Arg Trp Arg Ser
            115                 120                 125

CTT CGG AAA ATC TTG AAT TCT AAT ATT TTC TCT AGC AAC AGG CTT GAT       432
Leu Arg Lys Ile Leu Asn Ser Asn Ile Phe Ser Ser Asn Arg Leu Asp
        130                 135                 140

GCA AAT CAG CAT CTC AGG TCC CGA AAG ATA CAA GAG TTT ATT GAT TAT       480
Ala Asn Gln His Leu Arg Ser Arg Lys Ile Gln Glu Phe Ile Asp Tyr
145                 150                 155                 160

TGC CGA AAG TGT AGC CAA ACA GGG GAG GCA GTG AAT ATA GGC CAA GCT       528
Cys Arg Lys Cys Ser Gln Thr Gly Glu Ala Val Asn Ile Gly Gln Ala
                165                 170                 175

GCT TTT GAG ACC TCT ATT AAT TTA CTT TCC AAT ACT ATT TTC TCC AAG       576
Ala Phe Glu Thr Ser Ile Asn Leu Leu Ser Asn Thr Ile Phe Ser Lys
                180                 185                 190

GAT GTA GTC CAC CCT TAT GCA AAT TCA GAA TTC AAG GAT GTT GTT TGG       624
Asp Val Val His Pro Tyr Ala Asn Ser Glu Phe Lys Asp Val Val Trp
                195                 200                 205

AAA ATC ATG GAA GAA GCT GGT AAG CCA AAC TTG GCT GAT TAT TAC CCA       672
Lys Ile Met Glu Glu Ala Gly Lys Pro Asn Leu Ala Asp Tyr Tyr Pro
        210                 215                 220

ATC TTG GGA AAG ATT GAT CCT CAA GGG ATA AGG CGA CGC GTA GGC AAG       720
Ile Leu Gly Lys Ile Asp Pro Gln Gly Ile Arg Arg Arg Val Gly Lys
225                 230                 235                 240

TGT TTT GGT AAG TTG CTT CAG CAG ATT GAG GGA TTG ATT GAT CAA CGT       768
```

```
                Cys Phe Gly Lys Leu Leu Gln Gln Ile Glu Gly Leu Ile Asp Gln Arg
                                245                 250                 255

TTG CAG CAA AGG AAG AAA TTG CAA ACT GGC GAT AGT GCT GAT GTT CTT             816
Leu Gln Gln Arg Lys Lys Leu Gln Thr Gly Asp Ser Ala Asp Val Leu
            260                 265                 270

GAT GTT TTG TTA GAT ACT AGC CAA GAA GAT CCA CAT GCA ATT GAT AGA             864
Asp Val Leu Leu Asp Thr Ser Gln Glu Asp Pro His Ala Ile Asp Arg
            275                 280                 285

AAT CAT ATA GAG CGC TTG TGC ATG GAC CTT TTT ATT GCG GGG ACT GAT             912
Asn His Ile Glu Arg Leu Cys Met Asp Leu Phe Ile Ala Gly Thr Asp
290                 295                 300

ACA AGT TCA AAT ACA TTA GAA TGG GCA ATG GTT GAG ACC ATG AGG AAA             960
Thr Ser Ser Asn Thr Leu Glu Trp Ala Met Val Glu Thr Met Arg Lys
305                 310                 315                 320

CCA TAC ATA ATG AAA AAA GCT AAA AAC GAG CTA GCA GAA GTT ATT GGC            1008
Pro Tyr Ile Met Lys Lys Ala Lys Asn Glu Leu Ala Glu Val Ile Gly
                325                 330                 335

AAA GGC AGC GTA ATA GAA GAA GCT GAT ATT GGA CGT CTC CCT TAT TTG            1056
Lys Gly Ser Val Ile Glu Glu Ala Asp Ile Gly Arg Leu Pro Tyr Leu
                340                 345                 350

CAG TGC ATT GTT AAA GAA ACC TTA AGA ATA CAC CCA CCA GGT CCC TTT            1104
Gln Cys Ile Val Lys Glu Thr Leu Arg Ile His Pro Pro Gly Pro Phe
                355                 360                 365

TTA ATT CGC AAG GTT GAT CAA GAC GTT GAG GCG TGT GGC TAT TTT GTT            1152
Leu Ile Arg Lys Val Asp Gln Asp Val Glu Ala Cys Gly Tyr Phe Val
370                 375                 380

CCA AAA GAC TCT CAA GTG TTG GTG CAT ATA TGG TCA ATA GGC CGC GAC            1200
Pro Lys Asp Ser Gln Val Leu Val His Ile Trp Ser Ile Gly Arg Asp
385                 390                 395                 400

CCA ACT ATA TGG GAG GAT CCT TTG GTA TTT AAG CCC GAA AGA TTT TGG            1248
Pro Thr Ile Trp Glu Asp Pro Leu Val Phe Lys Pro Glu Arg Phe Trp
                405                 410                 415

GGT ACA AAA ATG GAC GTT CGT GGA CAA GAT TTT GAA CTC ATT CCA TTT            1296
Gly Thr Lys Met Asp Val Arg Gly Gln Asp Phe Glu Leu Ile Pro Phe
                420                 425                 430

GGT GCC GGA CGA AGA ATT TGC CCG GGA TTA CCT TTG GCA ACC AGG ACA            1344
Gly Ala Gly Arg Arg Ile Cys Pro Gly Leu Pro Leu Ala Thr Arg Thr
                435                 440                 445

TTA ACT GCA ATG TTG GGT TCA TTG TTG AAT TCA TTT GAT TGG AAA GTT            1392
Leu Thr Ala Met Leu Gly Ser Leu Leu Asn Ser Phe Asp Trp Lys Val
    450                 455                 460

GAA GGC CAT ATT GAA CCA GAA GAT TTG GAT GTG GAA GAA AAG TTT GGC            1440
Glu Gly His Ile Glu Pro Glu Asp Leu Asp Val Glu Glu Lys Phe Gly
465                 470                 475                 480

ATT ACC CTG GCG AGA TCA CGT TCT TTA CGA GCT GTA CCT ATT CCG CTA            1488
Ile Thr Leu Ala Arg Ser Arg Ser Leu Arg Ala Val Pro Ile Pro Leu
                485                 490                 495

TAAATATCCT CACCCAGATT CGCCATATAC ATTATTGTTG ACAAGATAAC ACCGAAAACT         1548

GAAGTATTGG GCGTCTTGAT CTTATAACTT TGTCATGAAT AATAGTGTTC CACATGTTAT         1608

AGTATATATT TATATTATGA TTTGTTACCA TAATAGTAAA GGTATTATTG TCCTTTGCAT         1668

ATATTATAAA TAAATGTCAG GAGTTCATAG TTATCAAAAA AAAAAAAAAA AAAA              1722

(2) INFORMATION FOR SEQ ID NO:2:

(i) SEQUENCE CHARACTERISTICS:
        (A) LENGTH: 452
        (B) TYPE: nucleic acid
        (C) STRANDEDNESS: double
        (D) TOPOLOGY: linear
```

(xi) SEQUENCE DESCRIPTION: SEQ ID NO: 2:

```
TTAACCTTAA CGTACACCGG GCCCTCAGCT AGGGGGGGAA AAAAATTTAT TAGGAATTTG      60

TAGCTCTCCC AATTAAAAAA AAAATTGTTG TTTCCAAAAT ACTTTTTATT TTGACCAAAC     120

TCTCCAAATT TCCTTAAAAG TGTTTTTCTC AAAGAAAAAA AAAATCCTTA GGTTCGGCAA     180

AAATTTGGCC AAATAGGCCA TTAGTGAGAC TAACCAAATT AAAGACCAAG TTGCAAAAAT     240

AGGCCTGGAA CTCACCGATC CCTCTTTTGT CATCAATTGT TATTATGTAA TACCATACAA     300

GACTTATTAG GACCTACCGG CTAAGTTCAC TAGACTTGAT CCAAGAATTA GGTGCACTAT     360

TAATTTCTTT TCCGCCTGTG TACTATTAAT TTTAAATCAG TATTTATATC CCTGCCTCAT     420

GGCTTGTTCA ACTAGGAAGA AAGAAGTAAA CA                                   452
```

(2) INFORMATION FOR SEQ ID NO:3:

(i) SEQUENCE CHARACTERISTICS:
        (A) LENGTH: 1761
        (B) TYPE: nucleic acid
        (C) STRANDEDNESS: double
        (D) TOPOLOGY: linear     (xi) SEQUENCE DESCRIPTION: SEQ ID NO: 3:

```
ATG ATT GAC TTT ACC AAT TAT CTT CTA GTC CTA TTT CGC GTA TAT ATC        48
Met Ile Asp Phe Thr Asn Tyr Leu Leu Val Leu Phe Arg Val Tyr IlE
 1               5                  10                  15

TTT TAT TTG GTC GAT TAT GCT CCA ATC TTT GTT TGC GTA TAT CTT GTT        96
Phe Tyr Leu Val Asp Tyr Ala Pro Ile Phe Val Cys Val Tyr Leu Val
                20                  25                  30

TCC AAG CTA GTT CAT TTT TCA TTC ATC GAG AGG TCC AAA CAG AAA ATC       144
Ser Lys Leu Val His Phe Ser Phe Ile Glu Arg Ser Lys Gln Lys Ile
            35                  40                  45

AAT CGA CTC CCT CCT GGT CCA AAA CAG TGG CCT ATT GTT GGC AAC CTT       192
Asn Arg Leu Pro Pro Gly Pro Lys Gln Trp Pro Ile Val Gly Asn Leu
        50                  55                  60

TTT CAA TTA GGG CAA TTG CCT CAC AGA GAC ATG GCT TCA TTT TGT GAT       240
Phe Gln Leu Gly Gln Leu Pro His Arg Asp Met Ala Ser Phe Cys Asp
 65                  70                  75                  80

AAA TAT GGA CCA TTG GTC TAC CTC CGA CTA GGT AAT GTT GAT GCT ATA       288
Lys Tyr Gly Pro Leu Val Tyr Leu Arg Leu Gly Asn Val Asp Ala Ile
                85                  90                  95

ACA ACA AAT GAT CCC GAA ATC ATA AGG GAA ATA CTT GTA CAA CAA GAC       336
Thr Thr Asn Asp Pro Glu Ile Ile Arg Glu Ile Leu Val Gln Gln Asp
                100                 105                 110

GAT ATT TTT GCG TCT AGA CCC AGG ACT CTT GCT GCC ATA CAT CTA GCT       384
Asp Ile Phe Ala Ser Arg Pro Arg Thr Leu Ala Ala Ile His Leu Ala
            115                 120                 125

TAT GGT TGT GGA GAT GTA GCA TTG GCT CCC TTA GGA CCA AAA TGG AAG       432
Tyr Gly Cys Gly Asp Val Ala Leu Ala Pro Leu Gly Pro Lys Trp Lys
        130                 135                 140

AGA ATG AGA AGA ATA TGT ATG GAA CAT TTG TTG ACA ACT AAA AGG CTC       480
Arg Met Arg Arg Ile Cys Met Glu His Leu Leu Thr Thr Lys Arg Leu
145                 150                 155                 160

GAG TCC TTT GGA AAG CAT CGG GCA GAT GAA GCC CAA AGC CTA GTT GAA       528
Glu Ser Phe Gly Lys His Arg Ala Asp Glu Ala Gln Ser Leu Val Glu
                165                 170                 175

GAT GTA TGG GCC AAG ACA CAA AAA GGA GAG ACA GTG AAC TTA AGG GAT       576
Asp Val Trp Ala Lys Thr Gln Lys Gly Glu Thr Val Asn Leu Arg Asp
                180                 185                 190

TTA TTA GGG GCT TTT TCA ATG AAC AAT GTA ACT AGG ATG TTG TTG GGA       624
```

```
Leu Leu Gly Ala Phe Ser Met Asn Asn Val Thr Arg Met Leu Leu Gly
            195                 200                 205

AAG CAA TTC TTT GGG GCA GAG TCA GCA GGG CCA CAA GAA GCA ATG GAA      672
Lys Gln Phe Phe Gly Ala Glu Ser Ala Gly Pro Gln Glu Ala Met Glu
    210                 215                 220

TTT ATG CAC ATA ACT CAT GAG TTA TTT TGG CTT CTT GGA GTG ATT TAT      720
Phe Met His Ile Thr His Glu Leu Phe Trp Leu Leu Gly Val Ile Tyr
225                 230                 235                 240

CTG GGT GAC TAT TTA CCT TTA TGG AGG TGG ATT GAC CCT CAT GGT TGT      768
Leu Gly Asp Tyr Leu Pro Leu Trp Arg Trp Ile Asp Pro His Gly Cys
                245                 250                 255

GAG AAG AAA ATG AGG GAA GTG GAG AAA AGG GTT GAT GAT TTT CAC ATG      816
Glu Lys Lys Met Arg Glu Val Glu Lys Arg Val Asp Asp Phe His Met
            260                 265                 270

AGA ATT ATT GAA GAA CAT AGA AAG AAC GGA AAA AAT GTT GAT GAA GGT      864
Arg Ile Ile Glu Glu His Arg Lys Asn Gly Lys Asn Val Asp Glu Gly
        275                 280                 285

GAA ATG GAC TTT GTT GAT GTT TTA TTG TCT TTG CCA GGT GAA GAT GAA      912
Glu Met Asp Phe Val Asp Val Leu Leu Ser Leu Pro Gly Glu Asp Glu
    290                 295                 300

GGA GAT GGG AAT GGA AAA CAA CAC ATG GAT GAC ACA GAG ATA AAA GCT      960
Gly Asp Gly Asn Gly Lys Gln His Met Asp Asp Thr Glu Ile Lys Ala
305                 310                 315                 320

CTA ATT CAG GAT ATG ATA GCT GCA GCC ACG GAT ACA TCT GCT GTC ACC     1008
Leu Ile Gln Asp Met Ile Ala Ala Ala Thr Asp Thr Ser Ala Val Thr
                325                 330                 335

AAC GAA TGG CCA ATG GCT GAG GTG ATA AAG CAT CCA AAT GTC CTC AAG     1056
Asn Glu Trp Pro Met Ala Glu Val Ile Lys His Pro Asn Val Leu Lys
            340                 345                 350

AAG ATC CAA GAA GAA CTT GAT ATT GTT GTT GGA TCG GAC CGT ATG GTA     1104
Lys Ile Gln Glu Glu Leu Asp Ile Val Val Gly Ser Asp Arg Met Val
        355                 360                 365

ACC GAA TCC GAC TTG GTT CAT CTC AAG TAC CTT CGT TGT GTA GTA CGT     1152
Thr Glu Ser Asp Leu Val His Leu Lys Tyr Leu Arg Cys Val Val Arg
    370                 375                 380

GAA ACA TTT CGA ATG CAC CCT GCT GGT CCA TTT CTA ATT CCA CAT GAA     1200
Glu Thr Phe Arg Met His Pro Ala Gly Pro Phe Leu Ile Pro His Glu
385                 390                 395                 400

TCA ATT CGA GAT ACT AAG ATC AAC GGC TAT TAT ATC CCA GCA AAG ACA     1248
Ser Ile Arg Asp Thr Lys Ile Asn Gly Tyr Tyr Ile Pro Ala Lys Thr
                405                 410                 415

CGT GTC TTC ATC AAC ACA CAT GGT CTT GGT AGA AAC ACA AAG ATA TGG     1296
Arg Val Phe Ile Asn Thr His Gly Leu Gly Arg Asn Thr Lys Ile Trp
            420                 425                 430

GAT AAT ATT GAT GAG TTT AGG CCA GAG AGA CAT TTG CCT GCA GAT GAA     1344
Asp Asn Ile Asp Glu Phe Arg Pro Glu Arg His Leu Pro Ala Asp Glu
        435                 440                 445

TTA AGT AGA GTT GAA ATA AGT CAT GGG GCA GAT TTC AAG ATT TTA CCA     1392
Leu Ser Arg Val Glu Ile Ser His Gly Ala Asp Phe Lys Ile Leu Pro
    450                 455                 460

TTT AGT GCT GGA AAA AGG AAG TGT CCT GGT GCA CCA TTA GGA GTG AAA     1440
Phe Ser Ala Gly Lys Arg Lys Cys Pro Gly Ala Pro Leu Gly Val Lys
465                 470                 475                 480

TTG GTA CTT ATG GCT TTG GCT AGA TTG TTC CAT TGC TTT GAG TGG AGC     1488
Leu Val Leu Met Ala Leu Ala Arg Leu Phe His Cys Phe Glu Trp Ser
                485                 490                 495

CCA CCA GAT GGA TTA CGG CCT GAA GAT ATT GAC ACA ATT GAG GTT TAC     1536
Pro Pro Asp Gly Leu Arg Pro Glu Asp Ile Asp Thr Ile Glu Val Tyr
            500                 505                 510
```

```
GGA ATG ACT ATG CCT AAA GCT AAG CCA TTG ATG GCT ATT GCT AGG CCT         1584
Gly Met Thr Met Pro Lys Ala Lys Pro Leu Met Ala Ile Ala Arg Pro
        515                 520                 525

CGA CTG CCT GAT CAC CTG TAC CAC TCA ATC AAA TGATTTATCA TTTCCTTATA       1637
Arg Leu Pro Asp His Leu Tyr His Ser Ile Lys *
    530                 535             539

CAAATTAAAA GTGTGTTATT AATAACTTTT TTAAGTAGTT GGACCATATA GTTATTTGTG       1697

TAGACAGATA CTAAAATATG ATACATCTCT TTTTCTGAAT CAATAAAAAA AAAAAAAAA       1757

AAAA                                                                   1761

(2) INFORMATION FOR SEQ ID NO:4:

(i) SEQUENCE CHARACTERISTICS:
        (A) LENGTH: 1041
        (B) TYPE: nucleic acid
        (C) STRANDEDNESS: double
        (D) TOPOLOGY: linear (xi) SEQUENCE DESCRIPTION: SEQ ID NO: 4:

GAAACAGCGC AGATACCAGT GCTGAAACGA TGCAGAAACA GTTTAAAACA ACGCAGATAC         60

ATTTCTGAAA CGATGCAGAA ACAGTTAGAT ACGGTGCTGC AGAAACAGTT GAAACGGTTC        120

AGAAACAGTT AGATACGGTG CTGCAGGAAC AGTTGAAACA ATGCAGAAAT AGTTGAGATA        180

CTGTGCTGCA GAAACAGTTG AAACGGTGCA GAAACAGTTG AGACACGGTG CTGCAGAAAC        240

AGTTGTAACG GTGCAGAAAC AGTTAGATAC GGTGCAGAAA TAATGAGATT CAACGAGATA        300

CATTGAGGAT GGATGAGGAA AAGTGAAATT GGGAATAATG AGAGGAGTAA AAGTGAAATT        360

GGGAGGAAAT GGTGAGAGGA AAAGTGAAAT ATGGGGAAAT GGGAGAAGCA AAAATGATAG        420

TCGGGGAAAT ATAAGAAGA ATGTAAGGGC TTGGTATGTT ATGGGAAAAT ATTGCTATGT         480

TTTTGCTATG TTTGCAATTA TCTTGTGTTT TCCTCTATAT AGGGTAATTT TACTAAAATG        540

TTGCTATGTT TGGTAATTAA GCTCTAAAAC TTGTACTTTT ATGTAAAAAT TCCTCGAGAT        600

AGCTTACAAC AACATATCCA ATGATATTCC ACCAATTTGG AATTTGGGGA GGGTAAAATG        660

TACGCAGACC TTGCCTCCAC TAAAATAGAA AAGTTGTTTT CAAAAGATCC TCGTTTAAAG        720

AAAATATTTT TTAAAAAATA AATTTAAAAA TATTTTGAAA ACATATTTAA AGTAAAACAA        780

TGATGAAAGA CTGAGATTAA GATAGGTTGT TCTTTCAAAT TTTCCAATAA TATCGGTCAT        840

GTGAAAGCAA TAAGCGTGAG TTCAAGATGA ATAGTGTAGT TGAAACATGT CAAGATGGTG        900

GGCTTCCTAA TCACTCGCGG TCATGTCTTT TTGCAGCCAA TTGCATATTG TTTAAACAGA        960

TTATAAATTA AGTAACATTT AACAACACAT TAATTACCTT ACTGAAGCTT GTAAACTACT       1020

TTTCCTCTTT GACAAATTAA G                                                1041

(2) INFORMATION FOR SEQ ID NO:5:

(i) SEQUENCE CHARACTERISTICS:
        (A) LENGTH: 23
        (B) TYPE: nucleic acid
        (C) STRANDEDNESS: double
        (D) TOPOLOGY: linear (xi) SEQUENCE DESCRIPTION: SEQ ID NO: 5:

AAAGAAACAT TTCGAAAGCA CCC                                                23

(2) INFORMATION FOR SEQ ID NO:6:

(i) SEQUENCE CHARACTERISTICS:
        (A) LENGTH: 25
```

(B) TYPE: nucleic acid
            (C) STRANDEDNESS: double
            (D) TOPOLOGY: linear (xi) SEQUENCE DESCRIPTION: SEQ ID NO: 6:

AAATTCTTCG TCCAGCACCA AATGG                                            25

(2) INFORMATION FOR SEQ ID NO:7:

(i) SEQUENCE CHARACTERISTICS:
            (A) LENGTH: 31
            (B) TYPE: nucleic acid
            (C) STRANDEDNESS: double
            (D) TOPOLOGY: linear (xi) SEQUENCE DESCRIPTION: SEQ ID NO: 7:

ATGAATTCAA AGAAACATTT CGAAAGCACC C                                     31

(2) INFORMATION FOR SEQ ID NO:8:

(i) SEQUENCE CHARACTERISTICS:
            (A) LENGTH: 33
            (B) TYPE: nucleic acid
            (C) STRANDEDNESS: double
            (D) TOPOLOGY: linear (xi) SEQUENCE DESCRIPTION: SEQ ID NO: 8:

ATAAGCTTAA ATTCTTCGTC CAGCACCAAA TGG                                   33

(2) INFORMATION FOR SEQ ID NO:9:

(i) SEQUENCE CHARACTERISTICS:
            (A) LENGTH: 30
            (B) TYPE: nucleic acid
            (C) STRANDEDNESS: double
            (D) TOPOLOGY: linear (xi) SEQUENCE DESCRIPTION: SEQ ID NO: 9:

AACTAAAATC AAGACAAGTA GTAATCCACC                                       30

(2) INFORMATION FOR SEQ ID NO:10:

(i) SEQUENCE CHARACTERISTICS:
            (A) LENGTH: 29
            (B) TYPE: nucleic acid
            (C) STRANDEDNESS: double
            (D) TOPOLOGY: linear (xi) SEQUENCE DESCRIPTION: SEQ ID NO: 10:

GTTGCTTATT GCTAGGTAAC GAATACTTG                                        29

(2) INFORMATION FOR SEQ ID NO:11:

(i) SEQUENCE CHARACTERISTICS:
            (A) LENGTH: 30
            (B) TYPE: nucleic acid
            (C) STRANDEDNESS: double
            (D) TOPOLOGY: linear (xi) SEQUENCE DESCRIPTION: SEQ ID NO: 11:

ACTCCCCTGC CCTTAATTGG TAATTTACAT                                       30

(2) INFORMATION FOR SEQ ID NO:12:

(i) SEQUENCE CHARACTERISTICS:
            (A) LENGTH: 30
            (B) TYPE: nucleic acid (C) STRANDEDNESS: double
        (D) TOPOLOGY: linear (xi) SEQUENCE DESCRIPTION: SEQ ID NO: 12:

AACACTCTTG GTGCTCAACC CCATCAGTCC                                30

(2) INFORMATION FOR SEQ ID NO:13:

(i) SEQUENCE CHARACTERISTICS:
        (A) LENGTH:  30
        (B) TYPE: nucleic acid
        (C) STRANDEDNESS: double
        (D) TOPOLOGY: linear (xi) SEQUENCE DESCRIPTION: SEQ ID NO: 13:

AACTCGAGGG TTACTATATA CCAAAAACAC                                30

(2) INFORMATION FOR SEQ ID NO:14:

(i) SEQUENCE CHARACTERISTICS:
        (A) LENGTH:  26
        (B) TYPE: nucleic acid
        (C) STRANDEDNESS: double
        (D) TOPOLOGY: linear (xi) SEQUENCE DESCRIPTION: SEQ ID NO: 14:

AAACAAAGAT TGGAGCATAA TCGACC                                    26

(2) INFORMATION FOR SEQ ID NO:15:

(i) SEQUENCE CHARACTERISTICS:
        (A) LENGTH:  26
        (B) TYPE: nucleic acid
        (C) STRANDEDNESS: double
        (D) TOPOLOGY: linear (xi) SEQUENCE DESCRIPTION: SEQ ID NO: 15:

TAGTTCATTT TTCATTCATC GAGAGG                                    26

(2) INFORMATION FOR SEQ ID NO:16:

(i) SEQUENCE CHARACTERISTICS:
        (A) LENGTH:  31
        (B) TYPE: nucleic acid
        (C) STRANDEDNESS: double
        (D) TOPOLOGY: linear (xi) SEQUENCE DESCRIPTION: SEQ ID NO: 16:

TATACGCGAA ATAGGACTAG AAGATAATTG G                              31

(2) INFORMATION FOR SEQ ID NO:17:

(i) SEQUENCE CHARACTERISTICS:
        (A) LENGTH:  29
        (B) TYPE: nucleic acid
        (C) STRANDEDNESS: double
        (D) TOPOLOGY: linear (xi) SEQUENCE DESCRIPTION: SEQ ID NO: 17:

AAACAGAAAA TCAATCGACT CCCTCCTGG                                 29

CYTOCHROME P450 GENE

FIELD OF THE INVENTION

The present invention relates to plant-derived novel cytochrome P450 genes. The present invention further relates to a cytochrome P450-derived promoter which functions at initial stages of flower-bud formation.

BACKGROUND OF THE INVENTION

Flower buds are formed in a period when higher plants convert their growth from vegetative growth to reproductive growth. In this period, many genes express as the functions and forms of the plants change. It is therefore of significant importance to obtain a gene expressed specifically at initial stages of flower-bud formation and its promoter to provide a means for clarifying the mechanism of reproductive growth and for genetically engineering plants in their reproductive growth period.

However, the mechanism of flower-bud formation has not been fully clarified, and, in particular, no gene that is involved in flower-bud formation or promoter that induces its expression are known.

On the other hand, cytochrome P450 in higher plants is known as a gene which is involved in 1. secondary metabolism of flavonoids and alkaloids, and 2. metabolism of chemicals such as herbicides. Examples of cytochrome P450 involved in the secondary metabolism include cDNA for cinnamate 4-hydroxylase, flavonoid-3'-5'-hydroxylase, jasmonate synthase, and salicylate hydroxylase which have been cloned and are known to be concerned with biophylaxis, and biosynthesis and metabolism of phytohormones and signal substances. It is known that cytochrome P450 genes consist of many groups of genes called superfamily, and it is also known that the homology of amino acid sequences in a family equals to, or more than 40% (Nebert et al. DNA Cell Biol. 10, 1–14, 1991). No presence of a cytochrome P450 that specifically expresses at initial stages of flower-bud growth has been known heretofore.

SUMMARY OF THE INVENTION

The present invention provides a cytochrome P450 expressed specifically at initial stages of flower-bud growth, a gene encoding the cytochrome P450, and a promoter which induces expression of the gene.

DETAILED DESCRIPTION OF THE INVENTION

The inventors found in studies on the mechanism of flower-bud formation that there are some cytochrome P450 enzymes in petunia that express specifically at the initial stages of flower-bud formation.

The gene of the present invention is a cytochrome P450 gene which expresses at the initial stages of flower-bud formation and that is obtained by cloning using Primer 1 (5'-AAAGAAACATTTCGAAAGCACCC), SEQ ID NO:5, and/or Primer 2 (5'-AAATTCTTCGTCCAGCACCAAATGG) SEQ ID NO:6. An example of the gene of the present invention is a cytochrome P450 gene encoding amino acid sequences encoded by the sequence having the nucleotide 1 to 1488 in SEQ ID NO: 1. Another example of the gene of the present invention is a cytochrome P450 gene encoding amino acid sequences encoded by the sequence having the nucleotide 1 to 1617 in SEQ ID NO: 3. The gene is a novel gene which belongs to a new family because its amino acid sequence has a 40% or lower sequence homology with amino acid sequences of known cytochrome P450, because its nucleotide sequence is different from the nucleotide sequences of any known cytochrome P450 genes, and because the site and time of its expression is specific.

The gene of the present invention is readily obtained by those skilled in the art according to the disclosure of the present specification. Leaves or flower buds of petunia (preferably those in the initial stage of growth) may be used as materials for isolation of the gene. For instance, following the procedures described in examples below, mRNA is purified at first from flower buds in the initial stage of growth, and single stranded cDNA is prepared using a reverse transcriptase. Primers for PCR are synthesized based on the amino acid sequences in the vicinity of the heme binding region in known cytochrome P450 (D. R. Nelson, Cytochrom P450, 2nd ed., p575–606, 1995). PCR was performed using the single strand cDNA as a template. The resulting PCR products were sequenced at random to provide a cDNA clone containing a partial nucleotide sequence of the cytochrome P450 (e.g. M15 and K40 in the examples below). A Northern blot analysis was carried out using the cDNA clone as a probe to confirm that the gene contained in the clone is most strongly expressed in initial stages of flower-bud growth. mRNA is purified from tissues in initial stages of flower-bud growth to construct a cDNA library. Screening the cDNA library with the previously acquired cDNA clone containing a partial nucleotide sequence of the cytochrome P450 can provide a full-length cDNA clone (e.g. IMT-1 and IMT-2 in the examples below).

The gene can be confirmed to be a cytochrome P450 gene by examining its sequence homology with known cytochrome P450 genes by comparing their nucleotide sequences, or by expressing the gene with a suitable expression vector in a suitable host, for example, yeast, then measuring the expressed protein with a reduced-type spectrum, a spectrum in the presence of carbon monoxide (Hideo Okawa, Saibo-Kogaku, 6, 72–78, 1987).

The so-called reverse genetic methods, such as 1. introducing to a plant a binary vector which transcripts a gene in an antisense direction to inhibit expression of the gene and examine the phenotype of the plant, or 2. introducing to a plant a binary vector which transcripts a gene in a sense direction to excessively express the gene and examine the phenotype of the plant are widely used to investigate the function of the gene or the activity of the enzyme encoded by the gene. For example, the resulting IMT-1 gene or IMT-2 gene may be inserted downstream of 35S promoter in a sense or antisense direction into a vector to create a binary vector, and the binary vector may be introduced into Petunia hybrida (Surfinia purple, Suntory Ltd.). Transformation of petunia is easy, and is a widely accepted practice.

Alternatively, the use of Petunia hybrida containing transposon dTphl provides a plant having an intended gene (e.g., IMT-1 or IMT-2) destroyed by transposon. An analysis of its phenotype allows us to know the function of the gene and the activity of the enzyme encoded by the gene (Koes, et al.

Proceedings of the 4th International Congress of Plant Molecular Biology, 2071, 1994).

At this point in time, the mechanism of the gene of the present invention to be expressed specifically at initial stages in flower-bud formation has not been fully clarified. However, it is presumed that a promoter naturally associating with the cytochrome P450 gene of the present invention may have a nature whereby it specifically induces expression at initial stages in flower-bud formation.

Consequently, the present invention also provides a promoter which naturally associates with the cytochrome P450 gene described above. The promoter is contained in the nucleotide 1 to 452 in SEQ ID NO: 2 or in the nucleotide 1 to 1041 in SEQ ID NO: 4. It may be readily understood that the least necessary region as a promoter is somewhat shorter than this. A promoter modified by insertion, substitution or deletion may have the substantially same promoter activity. Such modification can be made, for example, by site specific mutagenesis or suitable restriction enzyme digestion. Thus, the present invention also includes sequences made by modifying the nucleotide 1 to 452 in SEQ ID NO: 2 or modifying the nucleotide 1 to 1041 in SEQ ID NO: 4 with one or more insertion, substitution and/or deletion, as far as they have the promoter activity.

The promoter of the present invention is isolated generally together with the above-mentioned cytochrome P450 gene. For instance, the promoter can be obtained by cloning promoter sequences related to gene regulation of plasmids (e.g. IMT-1 or IMT-2) containing a full-length cytochrome P450 gene through the inverse PCR method.

It was found that the resulting cytochrome P450 genes belong to new families. This invention clarifies the mechanism of flower-bud growth and enables the application of the cloned gene and its promoter in controlling flowering.

In other words, the genes of the present invention are expected to affect the flowering time, the shape of a flower and so on in various ways by introducing the gene to an ornamental plant, because the genes express specifically at initial stages of flower-bud formation. The genes are introduced preferably functionally combined with the promoters of the present invention, but it is also possible to use another promoter or to use in combination other elements to control the expression as needed. Examples of the ornamental plant include rose, chrysanthemum, carnation, gerbera, petunia, torenia and verbena. The genes of the present invention are further expected to be used to preferably affect the quantity and time of harvesting crops by affecting the flowering of cultivated plants such as grains and fructificative plants. Examples of such plants include rice, wheat, barley, tomato and apple.

It is believed to be possible to introduce the promoters of the present invention which are functionally combined with any desired genes into a plant and to express the genes at initial stages of flower-bud formation in a time-specific manner. Thus, it is possible to introduce the promoter into the ornamental plants and cultured plants such as those described above combined with various genes to affect, for example, color, size, shape, flowering time, flowering inhibition, etc.

The genes can be introduced into a plant by transforming plant cells with a conventional method, e.g. a method using Agrobacterium tumefaciens. The plant cells containing the introduced genes can be selected using a suitable marker when the cells are transformed. The cells confirmed to have the intended gene introduced can be regenerated into plants. Methods are widely known for selecting plant strains which stably maintain the genotype of the introduced gene. See for example, S. C. Deroles, et al., Biotechnology of Ornamental Plants, p87–119, 1997, which describes these techniques.

Cytochromes P450, which express in initial stages in flower-bud formation like cytochromes P450 of the present invention and which have slightly different amino acid sequences or nucleotide sequences, may exist in plants other than petunia. These genes encoding cytochromes P450 can be isolated from plants by the methods described above. More readily, the genes may be isolated by creating cDNA libraries from mRNA extracted from flower buds of respective plants and screening by general methods using as a probe the sequence having the nucleotide 1 to 1488 in SEQ ID NO: 1 or a partial sequence consisting of at least 10 to 15 bases selected as needed therefrom. Therefore, the genes and promoters of the present invention include genes encoding the cytochrome P450 which hybridizes with the sequence having the nucleotide 1 to 1488 in SEQ ID NO: 1, the nucleotide 1–1617 in SEQ ID NO: 3, or a partial sequence consisting of at least 10 to 15 bases selected as needed therefrom and which express at initial stages in flower-bud formation in plants. Such hybridization can be carried out e.g. under stringent conditions including washing conditions of 6× SSC at 50° C.

The present invention further relates to cytochrome P450 which has the amino acid sequence of the amino acid sequence 1 to 496 in SEQ ID NO: 1. The protein can be extracted from petunia or other plants' flower buds at initial stages of formation. It is also possible to obtain the protein by inserting the gene of the present invention into a suitable expression vector, transforming a suitable host such as *E. coli* with the vector, culturing the transformed host, and purifying the protein from the cells or extracts. The purified protein can be used for flower-bud formation and controlling the form of flowers, etc.

The present invention provides a novel cytochrome P450 gene as well as a promoter thereof. The present invention has further enabled application of the cytochrome P450 gene and the promoter thereof for controlling plant flowering.

The invention will be described more specifically by following examples, which are not intended to limit the scope of the invention.

EXAMPLE 1

Purification of mRNA

Figure 1:
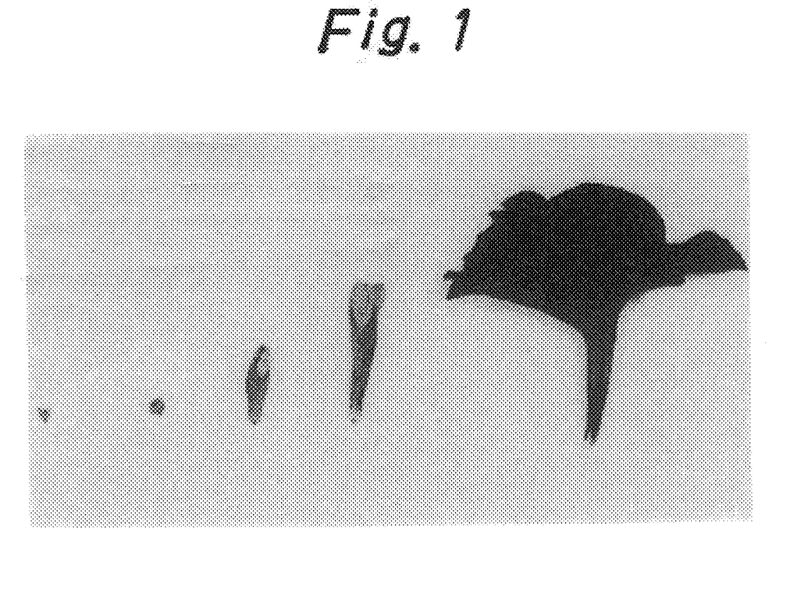
FIG. 1 is a photograph in place of a drawing showing the stages of flower-bud growth.

Seeds of Petunia hybrida Vilm™ (Sakata Inx Corp.) were sown on a vermiculite soil, and were budded and grown at 25° C. under 12-hour light and 12-hour dark conditions. After 100 days, flower-buds were sampled at different five stages of growth (see FIG. 1). mRNA was purified from 0.1 g of flower buds in each stage. QuickPrep Micro mRNA Purification Kit™ (Pharmacia) was used to purify mRNA following the manufacturer's recommended procedures.

EXAMPLE 2

Synthesis of Single Strand cDNA

Single strand cDNA was synthesized using as templates about 100 ng of the mRNA from each stage of flower buds in Example 1. First-strand CDNA Synthesis Kit™ (Pharmacia) was used to synthesize cDNA following the manufacturer's recommended procedures.

EXAMPLE 3

Synthesis of Primers for PCR and the PCR Conduct

First, Primers 1 and 2 were synthesized as primers for PCR. Recognition sites for restriction endonucleases were inserted to respective primers. The underlined show the recognition sites. The recognition sites are not limited to those shown here but use of other suitable recognition sites is allowed as needed.

```
                                         SEQ ID NO: 7
Primer 1' ;
5' -ATGAATTCAAAGAAACATTTCGAAAGCACCC,
   EcoRI
                                         SEQ ID NO: 8
Primer 2';
5' -ATAAGCTTAAATTCTTCGTCCAGCACCAAATGG,
   HindIII
```

Next, PCR was conducted. The reaction was conducted in 50 μl of a reaction fluid containing 0.14 pg/ml of the template single stranded cDNA (a mixture of those from stages 1 to 5) given in Example 2, 10 pmol of Primer 1', 10 pmol of Primer 2', 0.04 mM dNTP, 2.5 mM magnesium chloride, buffer for PCR (Toyobo Co., Ltd.), and 0.1 unit/μl of TaqDNA polimerase (Toyobo Co., Ltd.) The reaction mixture was maintained at 94° C. for 5 minutes, then were cycled 30 times between 94° C. for 1 minute, 40° C. for 1 minute and 72° C. for 3 minutes. Then it was kept at 4° C.

The PCR products were separated by electrophoresis on 2% agarose gel, then DNA fragments of about 250 bp were collected, cleaved with EcoRI and HindIII, then were cloned into the EcoRI site and HindIII site of the pBluescript SK (+) (Stratagene) to introduce into *E. coli* JM109.

EXAMPLE 4

Analysis of PCR Products

The *E. coli* JM109 prepared in Example 3 was transformed to give colonies, from which 40 colonies were picked out at random and cultured separately. Plasmid DNA was purified from each culture fluid, and the nucleotide sequence of the DNA was determined at random. This resulted in a clone (M15) which has a partial sequence of the cDNA of cytochrome P450.

EXAMPLE 5

Northern blot Analysis of Expression of M15 Gene

Figure 2:
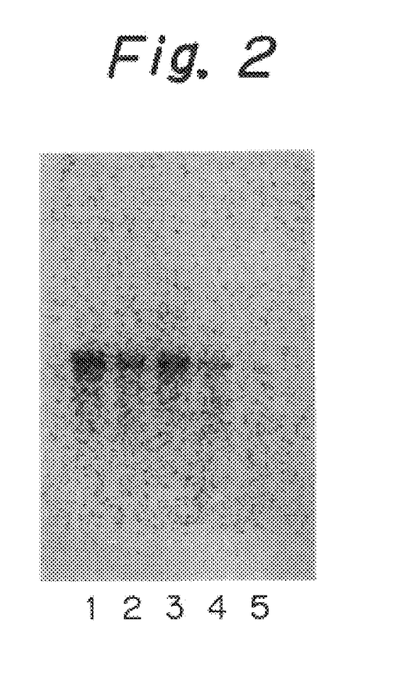
FIG. 2 shows a Northern blot analysis illustrating expression of M15 gene in each stage of the growth of flower-buds.

Expression of M15 gene in each stage of flower-buds (FIG. 1) was detected using $^{32}$P-labelled EcoRI-HindIII fragments of the M15 clone as a DNA probe. 0.3 μg of mRNA was used for the analysis. FIG. 2 shows the results. It was demonstrated from FIG. 2 that the maximum expression was obtained in stage 1.

EXAMPLE 6

Cloning CDNA for Cytochrome P450 expressed in Flower Buds

A cDNA library was constructed from the mRNA which was expressed at the stage 1 in the flower-bud growth. The library was constructed using ZAP-cDNA Synthesis Kit™ (Stratagene) following the manufacturer's recommended procedures. The Gigapack II Plus™ (Stratagene) was used for packaging.

About 300,000 cDNA clones were screened using $^{32}$P-labelled EcoRI-HindIII fragments of the M15 clone as a probe. Seven positive clones were selected. One clone that has the longest insert fragment (hereinafter referred to as IMT-1) was selected and was subjected to sequence analysis of cDNA. This resulted in cDNA encoding a novel full-length cytochrome P450 (SEQ ID NO.1). It was found that the amino acid sequence of the cytochrome P450 has 37% homology with the amino acid sequence of petunia flavonoid-3'-5'-hydroxylase.

EXAMPLE 7

Preparation of Template Genome DNA for Inverse PCR (IPCR)

Chromosome DNA was prepared from 0.5 g of petunia leaves using ISOPLANT™ (Nippon Gene). After completely digesting 1 μg of the chromosome DNA with HincII, a self ligation reaction was carried out using T4 DNA ligase to produce template genome DNA for IPCR.

EXAMPLE 8

Inverse PCR (IPCR)

First, four different primers for IPCR were synthesized:

A primer: 5'-AACTAAAATCAAGACAAGTAGTAATCCACC-3' (SEQ ID NO:9);

B primer: 5'-GTTGCTTATTGCTAGGTAACGAATACTTG-3' (SEQ ID NO:10);

C primer: 5'-ACTCCCCTGCCCTTAATTGGTAATTTACAT-3' (SEQ ID NO:11); and

D primer: 5'-AACACTCTTGGTGCTCAACCCCATCAGTCC-3' (SEQ ID NO:12).

All the primers are positioned in the vicinity of the 5' end of IMT-1.

Next, PCR amplification was performed twice. The first PCR amplification was conducted in 50 μl of a reaction mixture. The reaction mixture contained 10 ng/μl of the template genome for IPCR obtained in Example 7 as well as 10 pmol of B primer, 10 pmol of C primer, 0.04 mM of dNTP, 2.5 mM of magnesium chloride, buffer for PCR (Toyobo Co., Ltd.), and 0.1 unit/μl of TaqDNA polimerase (Toyobo Co., Ltd.). The reaction mixture was maintained at 94° C. for 5 minutes, then were cycled 30 times between 94° C. for 1 minute, 55° C. for 2 minutes and 72° C. for 3 minutes. Then it was kept at 4° C.

The second PCR amplification was conducted in 50 μl of a reaction mixture. The reaction mixture contained 0.1 ng/μl of the product from the first IPCR, 10 pmol of A primer, 10 pmol of D primer, 0.04 mM of dNTP, 2.5 mM of magnesium chloride, buffer for PCR (Toyobo Co., Ltd.), and 0.1 unit/μl of TaqDNA polimerase (Toyobo Co., Ltd.). The reaction mixture was maintained at 94° C. for 5 minutes, then were cycled 30 times between 94° C. for 1 minute, 55° C. for 2 minutes and 72° C. for 3 minutes. Then it was kept at 4° C.

EXAMPLE 9

Cloning IPCR Products and DNA Sequence Determination

The products from the second IPCR were separated on a 0.7% agarose gel, and a 1.2-kb DNA product was specifically amplified and cloned into pTBlue T-Vector™ (Novagen). The plasmid was used to transform *E. coli* JM109. Seven single clones were cultured and subjected to DNA sequence determination. The sequence of the promoter region of IMT-1 was determined. The gene sequence of the promoter region of IMT-1 is shown in SEQ ID NO: 2 of sequence listing.

EXAMPLE 10

PCR and Analysis of PCR Products

PCR was further conducted using the PCR products obtained in Example 3. One nanogram of the PCR products and 70 pmol of each of primer 2' and primer 3 were reacted in 50 µl of a reaction mixture containing 0.2 mM dNTP, 2.5mM $MgCl_2$, buffer for PCR (Toyobo Co., Ltd.), and 0.1 unit/ml of rTaqDNA polimerase (Toyobo Co., Ltd.). The reaction mixture was maintained at 94° C. for 3 minutes, then were cycled 40 times between 94° C. for 30 seconds, 50° C. for 30 seconds and 72° C. for 45 seconds. Then it was cooled to 4° C.

The sequence of the primer 3 is shown below:

```
                                              (SEQ ID NO: 13)
Primer 3: 5'-AACTCGAGGGTTACTATATACCAAAAACAC
              XhoI
```

The resulting PCR products were separated by electrophoresis on a 2% agarose gel, then the DNA fragments of approximately 200 bp were collected, cloned into the XhoI site and HindIII site of pBluescriptSK+ plasmid vector, and introduced into *E. coli* JM109.

From the resulting transformed colonies, 22 clones were selected at random and their plasmids were extracted and sequenced. A clone (K40) which has the cDNA sequence of cytochrome P450 was obtained.

EXAMPLE 11

Northern blot Analysis showing Expression of K40 Gene

Figure 3:
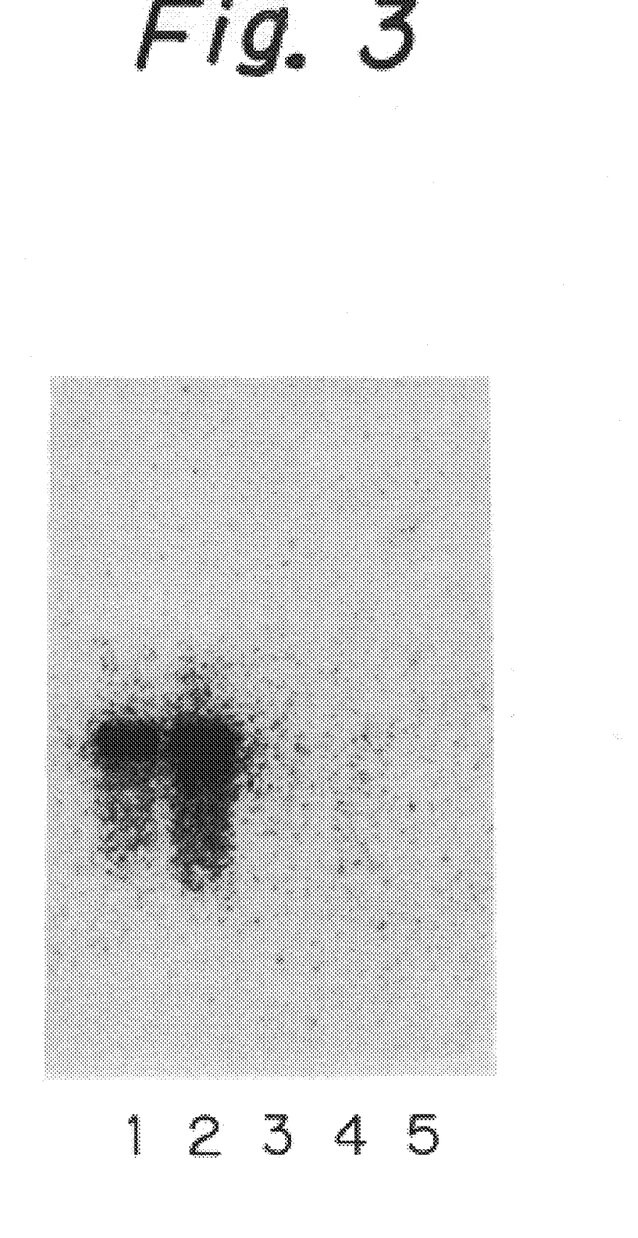
FIG. 3 shows a Northern blot analysis illustrating expression of K40 gene in each stage of the growth of flower-buds.

Expression of K40 gene in each stage of flower-buds (FIG. 1) was detected using $^{32}$P-labelled XhoI-HindIII fragments of the K40 clone as a DNA probe. 0.5 µg of mRNA was used for the analysis. FIG. 3 shows the results. It was demonstrated from FIG. 3 that the maximum expression was obtained in stage 2.

EXAMPLE 12

Cloning cDNA for Cytochrome P450 expressed in Flower Buds

A cDNA library was constructed from the mRNA which expressed at stage 2 in the flower-bud growth. The library was constructed using ZAP-cDNA Synthesis Kit™ (Stratagene) following the manufacturer's recommended procedures. The Gigapack II Plus (Stratagene) was used for packaging.

About 500,000 cDNA clones were screened using $^{32}$P-labelled XhoII-HindIII fragments of the K40 clone as a probe. Ninety-three positive clones were selected. One clone that has the longest insert fragment was selected and was subjected to sequence analysis of cDNA. This resulted in cDNA (SEQ ID NO: 3) encoding a novel full-length cytochrome P450 (IMT-2). It was found that the amino acid sequence of the cytochrome P450 has 39% homology with the amino acid sequence of CYP71A1, a molecular species of cytochrome P450 from avocado.

EXAMPLE 13

Preparation of Template Genome DNA for IPCR

Chromosome DNA was prepared from 0.5 g of petunia leaves using ISOPLANT™ (Nippon Gene). After completely digesting 1 µg of the DNA with XbaI, self ligation was performed using T4 DNA ligase to produce template genome DNA for IPCR.

EXAMPLE 14

IPCR

In order to obtain the promoter of IMT-2, four different primers were synthesized:

E primer: 5'-AAACAAAGATTGGAGCATAATCGACC-3' (SEQ ID NO:14);

F primer: 5'-TAGTTCATTTTTCATTCATCGAGAGG-3' (SEQ ID NO:15);

G primer: 5'-TATACGCGAAATAGGACTAGAAGATAATTGG-3' (SEQ ID NO:16); and

H primer: 5'-AAACAGAAAATCAATCGACTCCCTCCTGG-3' (SEQ ID NO:17).

All the primers are positioned in the vicinity of the 5' end of IMT-2.

Next, PCR amplification was performed twice. The first PCR amplification was conducted in 50 µl of a reaction mixture. The reaction fluid contained 10 ng/µl of the template genome DNA for IPCR, 50 pmol of E primer, 50 pmol of F primer, as well as 0.2 mM of dNTP, 2.5 mM of magnesium chloride, buffer for PCR™ (Expand High Fidelity PCR System™, Boehringer Mannheim), and 0.04 unit/µl of enzyme mixes (Expand High Fidelity PCR System, Boehringer Mannheim). The reaction mixture was maintained at 94° C. for 5 minutes, then were cycled 30 times between 94° C. for 1 minute, 60° C. for 1 minute and 72° C. for 3 minutes. Then it was kept at 4° C.

The second PCR amplification was conducted in 50 µl of a reaction mixture. The reaction mixture contained 0.2 ng/µl of the product from the first IPCR, 50 pmol of G primer, 50 pmol of H primer, 0.2 mM of dNTP, 2.5 mM of magnesium chloride, buffer for PCR (Expand High Fidelity PCR System™, Boehringer Mannheim), and 0.04 unit/µl of enzyme mixes (Expand High Fidelity PCR System™, Boehringer Mannheim). The reaction mixes were maintained at 94° C. for 5 minutes, then were cycled 30 times between 94° C. for 1 minute, 60° C. for 1 minute and 72° C. for 3 minutes. Then it was kept at 4° C.

EXAMPLE 15

Cloning IPCR Products and DNA Nucleotide Sequence Determination

The products from the second IPCR were nucleotide separated on a 0.7% agarose gel, and a 1.7-kb DNA product was specifically amplified and cloned into pT7Blue T-Vector™ (Novagen). The plasmid was used to transform *E. coli* JM109. Single clones were cultured and subjected to DNA nucleotide sequence determination. The sequence of the promoter region of IMT-2 was determined. The gene sequence of the promoter region of IMT-2 is shown in SEQ ID NO: 4.

What is claimed is:

1. An isolated cytochrome P450 gene comprising a nucleotide sequence encoding the amino acid sequence of SEQ ID NO:1.

2. An isolated cytochrome P450 gene comprising a nucleotide sequence encoding the amino acid sequence of SEQ ID NO:3.

3. An isolated DNA which comprises a nucleotide sequence of SEQ ID NO: 2 or SEQ ID NO. 4.

* * * * *